United States Patent [19]

Fard

[11] Patent Number: 5,779,702
[45] Date of Patent: Jul. 14, 1998

[54] HIGH SPEED PULSE LAVAGE SURGICAL HAND TOOL ATTACHMENT

[75] Inventor: Mike Fard, Charlottesville, Va.

[73] Assignee: Microaire Surgical Instruments, Inc., Charlottesville, Va.

[21] Appl. No.: 838,534

[22] Filed: Apr. 9, 1997

[51] Int. Cl.⁶ .................................... A61B 17/56
[52] U.S. Cl. ...................... 606/53; 606/1; 604/30
[58] Field of Search ..................... 606/1, 53, 86, 606/80; 604/27, 30, 33, 36, 280, 283

[56] References Cited

U.S. PATENT DOCUMENTS

| | | | |
|---|---|---|---|
| 3,749,090 | 7/1973 | Stewart | 604/33 |
| 4,180,074 | 12/1979 | Murry et al. | 604/31 |
| 4,289,131 | 9/1981 | Mueller | 606/1 |
| 4,715,848 | 12/1987 | Beroza | 604/35 |
| 4,973,247 | 11/1990 | Varnes et al. | 433/85 |
| 5,037,423 | 8/1991 | Kenna | 606/88 |
| 5,125,837 | 6/1992 | Warrin et al. | 433/98 |
| 5,203,697 | 4/1993 | Malmin | 433/81 |

Primary Examiner—Guy V. Tucker
Attorney, Agent, or Firm—Whitham, Curtis & Whitham

[57] ABSTRACT

A pulsed lavage attachment (40) is secured to a conventional, powered, modular, surgical hand piece (42) to allow a pulsed lavage delivery set (18) to be connected to and controlled by the hand piece (42), thereby eliminating the need for dedicated air or power lines and a dedicated pulsed lavage hand piece in the operating room. The pulsed lavage attachment (40) includes an internal driver (52) which mates with an output driver of the hand piece (42) and is axially rotatable by the output driver. A cam driver (56) connected to the internal driver (52) by pegs or other suitable means, and is rotatable therewith, has a cammed surface (62). A bearing member (64) rides on the cammed surface (62), and drives shaft (66) in an axial direction. Membrane (68) flexes outward to actuate a connecter (24) of the pulsed lavage delivery set (18) to actuate an internal pumping cartridge therein.

6 Claims, 3 Drawing Sheets

HIGH SPEED PULSE LAVAGE SURGICAL HAND TOOL ATTACHMENT

DESCRIPTION

BACKGROUND OF THE INVENTION

1. Field of the Invention

The invention is generally related to powered hand tools used in surgical operations and, more particularly, to hand tools used for high speed pulsed lavage and to modular, powered surgical hand tool systems used in hospital operating rooms or similar environments.

2. Background Description

High speed pulse lavage instruments are used in the surgical setting for debriding bone surfaces as well as cleansing trauma and other soft tissue wounds. For example, in total hip and total knee operations, the high speed pulse lavage instrument is used to remove bone chips and debris during the surgical procedures. High speed pulse lavage instruments typically comprise a pulse lavage handpiece, water or lavage fluid delivery tubing equipped with a flow cut-off valve such as external tubing clamp, a connector fitted to the end of the delivery tubing which has an internal pump cartridge and fits within a coupler on the pulse lavage hand piece, and one or more disposable attachment nozzles that are selectively connectable to the connector, and related equipment such as splash shields. The connector fits within a round depression in the hand piece coupler and is held firmly in place by having external tabs on the connector fit within a slotted region on the coupler. The attachment nozzles include a length of tubing and an attached spray head tip which can provide single-stream, multiple-orifice, or shower head discharge of water. The length of tubing for the attachment nozzles can vary depending on the needs of the surgeon and the operation being performed, and can include bent regions for ease in directing the pulsed discharge of water. A surgeon may use one or more attachment nozzles during a single surgical procedure; thus, the attachment nozzles are disposable and are equipped with a quick-connect or other fitting which allows them to be attached and removed from the connector while it is installed within the hand piece coupler.

Pulsed lavage fluid delivery is achieved by the pulse lavage hand piece driving a membrane positioned within the coupler back and forth, which, in turn, drives a membrane positioned at the base of the connector back and forth. This back and forth movement pumps lavage fluids through the lavage fluid delivery tubing and out the tip of the attachment nozzle. Typically, a pulse lavage hand piece can provide a lavage fluid flow rate of several hundred milliliters per minute at a discharge of several thousand pulses per minute, and at an output pressure of several pounds per square inch (psi). An example of a pulse lavage hand piece is the air-powered, Microaire® 4740-000, which provides a flow rate of 500 ml/min. at 3000 pulses/min., and at a pressure of 6 psi/7 bars. Varying flow rates and output pressures can be achieved by the surgeon selectively driving the hand piece at different speeds, and by using different connectors with different pumping parameters.

Modular surgical hand piece systems have been developed for reducing the number of powered tools and drive lines required in the operating room. The intent of these modular systems is to allow the surgeon to perform multiple functions with a single powered hand piece. Currently, modular systems are commercially available from Microaire®, 3M®, Sodem systems®, Stryker®, and Zimmer®, and these modular systems allow multiple attachments to be selectively connected to a single powered hand piece for performing diverse procedures such as drilling, reaming, setting fixation pins, and driving a wide range of different saw blades. However, until this invention, no modular system has been developed which allows the same hand piece used for drilling, fixating, sawing, and reaming, to also be used for high speed pulsed lavage. Thus, an extra air hose or other power line is currently required in the operating room for operating the high speed pulse lavage. It would be advantageous to eliminate the need for additional air hoses and powered hand pieces by providing an attachment which is connectable to modular hand piece systems for driving a high speed pulsed lavage.

SUMMARY OF THE INVENTION

It is an object of this invention to provide an attachment for a modular surgical hand piece which allows the hand piece to be used for high speed pulsed lavage.

According to the invention, an attachment that allows modular surgical hand pieces to be used for high speed pulsed lavage includes a connector end which fits within the coupler of the hand piece, an internal drive train and cam drive for translating rotational drive power from the hand piece into axial movement of a membrane positioned at the opposite end of the attachment, and a coupler for connecting the membrane fitted connector end of a lavage fluid supply line. The attachment allows the surgeon to use the same powered surgical hand piece and drive line used for drilling, pin fixation, reaming, sawing, and other surgical procedures, to also be used for high speed pulsed lavage simply be removing an attached surgical tool from the hand piece, attaching the high speed pulsed lavage attachment to the hand piece, and connecting the lavage supply line and attachment nozzles.

BRIEF DESCRIPTION OF THE DRAWINGS

The foregoing and other objects, aspects and advantages will be better understood from the following detailed description of the preferred embodiments of the invention with reference to the drawings, in which.

DETAILED DESCRIPTION OF THE PREFERRED EMBODIMENTS OF THE INVENTION

Figure 1:
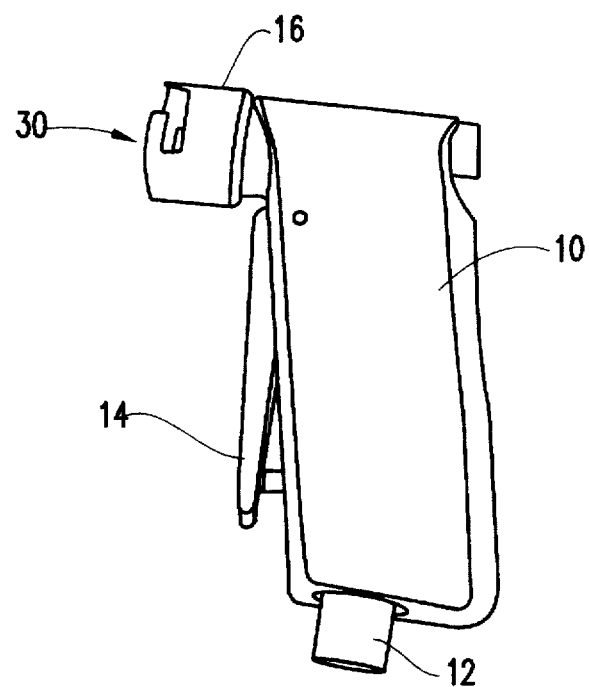
FIG. 1 is a side view of a prior art high speed pulsed lavage hand piece.

FIG. 1 shows the Microaire® 4740-000 pulse lavage hand piece 10 described in detail above. This hand piece includes an air hose connection 12, a trigger mechanism 14 for driving the high speed pulse lavage at varying speeds, and a coupler 16 for securing the connector end end of a lavage fluid supply line.

Figure 2:
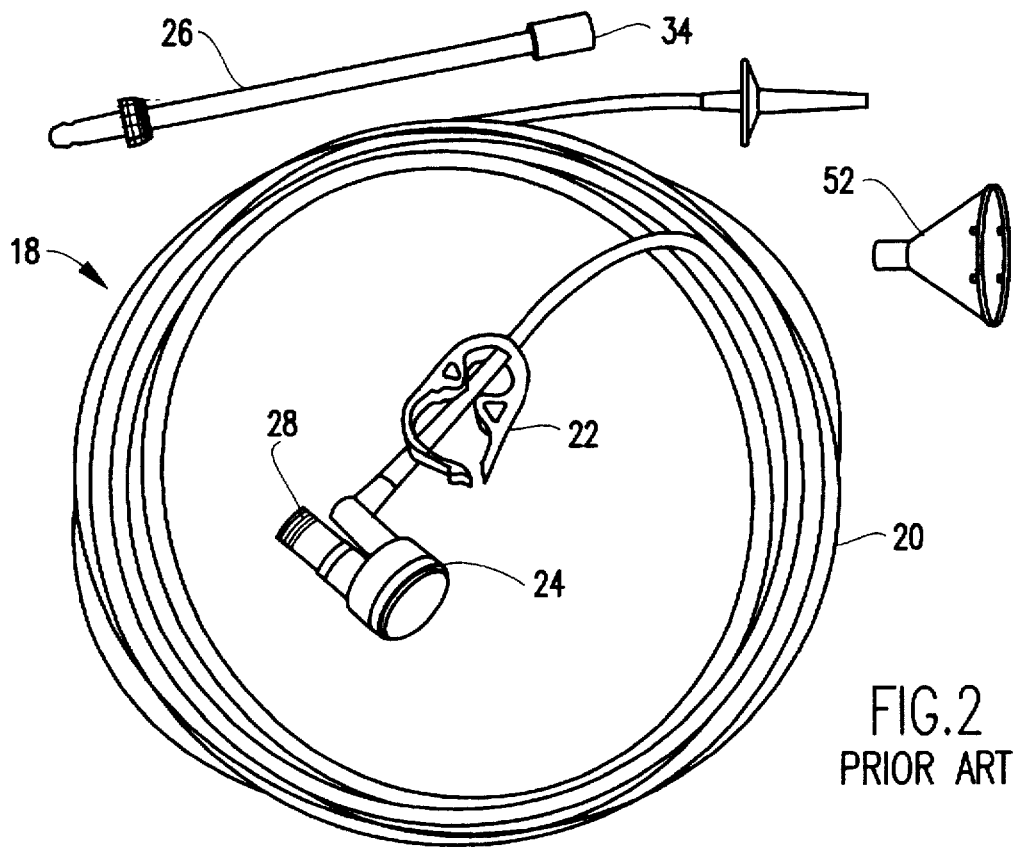
FIG. 2 is a top view of a prior art general surgery set used for a high speed pulsed lavage which includes a lavage fluid delivery tubing fitted with a control valve and connector, and separate disposable attachment nozzles and splash guards.

FIG. 2 shows a pulsed lavage fluid delivery set 18, such as the Microaire® 4740-020 general surgery set, which is used in conjunction with the Microaire® 4740-000 pulse lavage hand piece 10 shown in FIG. 1. The pulsed lavage fluid delivery set 18 includes a lavage fluid supply tubing 20 with an attached external clamp 22 for stopping the flow of fluid through the tubing 20, and an attached connector 24 with an internal pump cartridge which mates with the coupler 16 of the prior art high speed pulsed lavage hand piece shown in FIG. 1. In the Microaire® pulsed lavage system, tabs or outward projections (not shown) on the exterior sidewalls of the connector 24 fit within the slotted region 30 of the coupler 16. However, it should be understood that different mechanisms can be used for joining the connector 24 to the coupler 16. One or more attachment nozzles 26 are selectively connectable to the nozzle shaft 28 of the connector 24, and an array of different splash guards 32 or other attachments are connectable to the tip 34 of the attachment nozzles 26 depending on the needs of the surgeon and the operation being performed.

Pulsed lavage is achieved with the hand piece shown in FIG. 1 and the pulsed lavage fluid delivery set 18 (or equivalent tubing assembly for lavage fluid delivery) by the surgeon affixing the connector 24 to the hand piece 12, and connecting an appropriate nozzle attachment 26 to the nozzle shaft. Fluid flow results when the trigger mechanism 14 is actuated which causes back and forth pumping movements to be achieved in the internal pump cartridge of the connector 24, and this results in a pulsed lavage being discharged from the tip 34 of the attachment nozzle 26.

There are several competing pulsed lavage systems to those shown and discussed in connection with FIGS. 1 and 2. However, the problem with all of the prior art pulsed lavage systems is that they require their own hand piece 10 and their own air or other power line.

This invention seeks to utilize new or existing lavage pulsed lavage fluid delivery sets 18 which are the same as or similar to that shown in FIG. 2 in a modular surgical hand piece environment; rather than the dedicated hand piece 10 shown in FIG. 1. In this invention, the pulsed lavage fluid delivery set 18 needs a connector 24 with a built in pump cartridge which can be operated by a reciprocating membrane, attached tubing or other lavage fluid supply lines, and a nozzle outlet which can have an attached or selectively attachable nozzle attachment. The prior art system shown in FIG. 2 can be used in conjunction with this invention, however, it will be understood by those of skill in the art that the components of the pulsed lavage fluid delivery set 18 can be varied.

Figure 3:
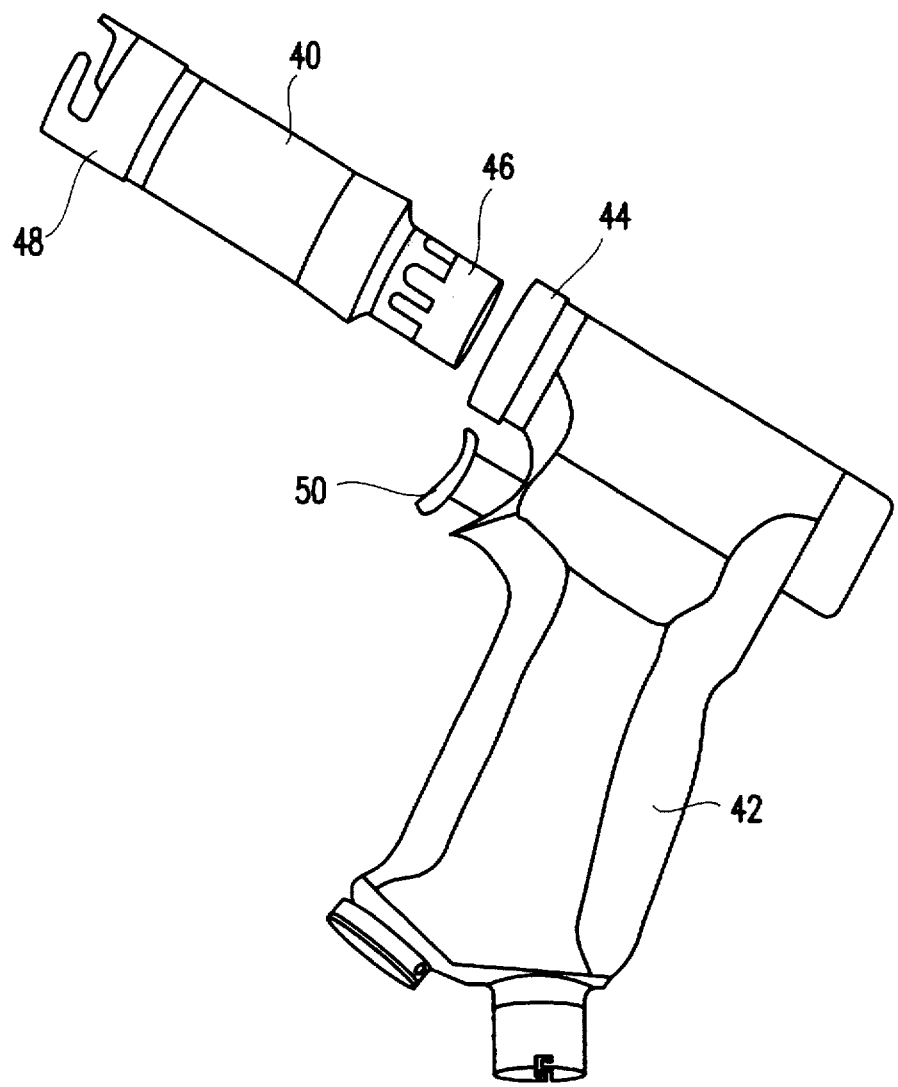
FIG. 3 is a side view of the modular attachment of this invention positioned adjacent a powered, modular surgical hand piece.

FIG. 3 shows the pulsed lavage attachment 40 of the present invention which is connectable to a powered, modular surgical hand piece 42. Suitable powered, modular surgical hand pieces 42 for use in conjunction with the pulsed lavage attachment 40 of this invention includes the MicroAire® 7100 Drill Reamer and the MicroAire® 6640 or 6640E SmartDriver™. However, it should be understood that the pulsed lavage attachment 40 is intended for application to any powered modular surgical hand piece 42 that is used for performing multiple functions such as pin fixation, drilling, reaming, sawing, etc. where operating tools (e.g., chucks for pin driving, drilling or shaping with a burr, and oscillating drivers for saw blades) are selectively connected to a coupler 44 on the hand piece 42. All that is required is that the pulsed lavage attachment 40 include a connector end 46 which fits within the coupler 44, a coupler end 48 that is selectively joinable to a connector 24 of a pulsed lavage fluid delivery set 18 (shown in FIG. 2), and an internal drive mechanism which translates the rotational drive power from the hand piece 42 into axial movement of a membrane positioned within the coupler 48 of the attachment. Similar to the coupler 16, shown in FIG. 1, the membrane within the coupler 48 moves back and forth at varying speeds under the control of trigger mechanism 50 in the modular hand piece 42, and actuates the internal pumping cartridge in the pulsed lavage fluid deliver set 18. The coupler 48 can have the same slotted outer configuration as the coupler 16 so that it can be joined to the connectors of existing pulsed lavage fluid delivery sets; however, the configuration of the coupler 48 can be varied to join with other pulsed lavage fluid delivery set configurations. All that is required is that the coupler 48 be able to securely hold a connector 24 with an internal pumping cartridge and transmit axial movement of a membrane in the coupler 48 to the pumping mechanism of the connector 24.

Figure 4:
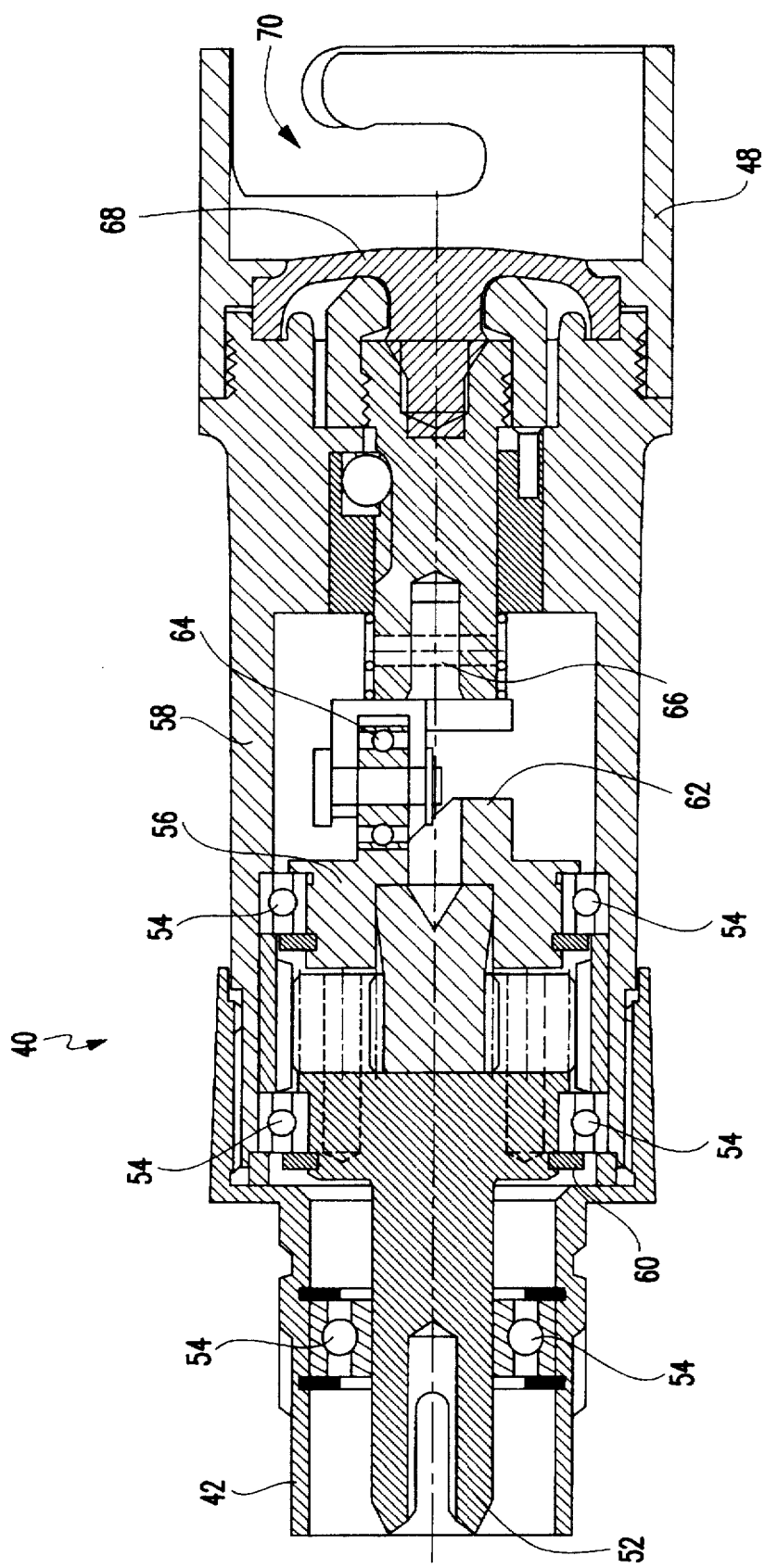
FIG. 4 is a cross-sectional view of the modular attachment of this invention.

FIG. 4 shows the preferred embodiment of the attachment 40 of the present invention. The connector end 42 includes an internal driver 52 which mates with a drive device in the modular hand piece 42 (shown in FIG. 3). The configuration of the internal driver 52 will vary depending on the drive device in the modular hand piece 42, and is principally designed to function as a connection with the drive device that allows rotational movement of the drive device to be transmitted to the internal driver 52. Ball bearings 54 or similar bearing elements allow the internal driver 52 to freely rotate a cam driver 56 secured to the end of the internal driver 52 within a housing 58 of the attachment 40. A retaining ring 60 can be used to help hold the cam driver/internal driver in place within the housing.

The cam driver 56 has a generally cylindrical configuration with an inclined surface 62 which bears against a wheel, surface, or ball bearing member 64 at the end of a lavage shaft pumping assembly 66. As the cam driver 56 rotates, the member 64 moves along inclined surface 62 of the cam driver 56 and moves the lavage shaft pumping assembly 66 axially back and forth. A membrane 68 connected to the lavage shaft pumping assembly 66 is caused to move or flex in and out at the coupler end 48 of the attachment 40 as the internal driver 52 rotates. Axial movement of the membrane 68 actuates an internal pumping cartridge of a connector for a pulsed lavage delivery set, such as that shown in FIG. 2, when it is attached. As discussed above, the connector can be secured to the coupler end 48 using a slot 70 or other suitable joining configuration.

Thus, when a surgeon requires high speed pulsed lavage, he or she simply connects the pulsed lavage attachment 40 of this invention to the modular hand piece he or she is or was previously using, and then attaches a pulsed lavage delivery set in the coupler end 48 of the attachment. Actuation of a trigger 50 or similar mechanism on the hand piece 42, causes rotational forces to be delivered to the internal driver 52, and these rotational forces, in turn, cause forward and rearward axial movement of a membrane 68 in the coupler end 48 via the cam driver 56, and the axial movement of the membrane 68 actuates the internal pumping mechanism of the attached pulsed lavage delivery set such that high speed pulsed lavage is delivered to the site required. The pulsed lavage attachment 40 of the present invention thus eliminates the need for a separate drive line (which can be an air hose or electrical line depending on the hand piece used) and a separate dedicated pulse lavage hand piece in the operating room.

While the invention has been described in terms of its preferred embodiments, those skilled in the art will recognize that the invention can be practiced with modification within the spirit and scope of the appended claims.

I claim:

1. A pulsed lavage attachment for a powered modular surgical hand piece, comprising:

a housing;

a connector located at a first end of said housing, said connector being configured to fit within a coupler of a powered modular surgical hand piece;

an internal driver positioned within said connector for mating with an output driver of a powered modular surgical hand piece, said internal driver being axially rotatable;

a coupler located at a second end of said housing, said coupler being configured to receive a connector of a pulsed lavage fluid delivery set;

an actuator positioned within said coupler, said actuator being axially moveable within said coupler to interact with a connector of a pulsed lavage fluid delivery set; and a drive mechanism which is connected to said internal driver in said connector and said actuator in said coupler which translates rotational drive power of said internal driver into axial movements of said actuator.

2. The pulsed lavage attachment of claim 1 wherein said drive mechanism includes:

a cam driver connected to said internal driver and rotatable therewith, said cam driver having a cam surface;

a shaft connected to said actuator; and a member connected to said shaft which rides on said cam surface of said cam driver.

3. The pulsed lavage attachment recited in claim 1 wherein said actuator includes a membrane which flexes in an axial direction.

4. The pulsed lavage attachment recited in claim 1 further comprising bearings positioned between said internal driver and said housing.

5. The pulsed lavage attachment recited in claim 1 further comprising bearings positioned between said internal driver and said connector.

6. The pulsed lavage attachment recited in claim 1 wherein said coupler located at said second end of said housing includes a slotted region.

* * * * *